United States Patent [19]

Duggan et al.

[11] Patent Number: 6,040,311
[45] Date of Patent: Mar. 21, 2000

[54] INTEGRIN RECEPTOR ANTAGONISTS

[75] Inventors: Mark E. Duggan, Schwenksville; George D. Hartman, Lansdale, both of Pa.

[73] Assignee: Merck & Co., Inc., Rahway, N.J.

[21] Appl. No.: 09/362,528

[22] Filed: Jul. 28, 1999

Related U.S. Application Data

[60] Provisional application No. 60/094,478, Jul. 29, 1998.

[51] Int. Cl.⁷ ................. A61K 31/505; A61K 31/435; C07D 239/42; C07D 471/04
[52] U.S. Cl. ................. 514/275; 514/300; 514/395; 514/398; 544/332; 546/122; 548/308.7; 548/321.5
[58] Field of Search ............ 544/332; 546/122; 548/308.7, 321.5; 514/275, 300, 395, 398

[56] References Cited

U.S. PATENT DOCUMENTS

| | | | |
|---|---|---|---|
| 5,204,350 | 4/1993 | Egbertson et al. | 514/255 |
| 5,217,994 | 6/1993 | Egbertson et al. | 514/484 |
| 5,741,796 | 4/1998 | Hartman et al. | 514/300 |
| 5,760,028 | 6/1998 | Jadhav et al. | 514/211 |
| 5,843,906 | 12/1998 | Chandrakumar et al. | 514/19 |
| 5,929,120 | 7/1999 | Hartman et al. | 514/634 |

FOREIGN PATENT DOCUMENTS

| | | |
|---|---|---|
| WO 95/32710 | 12/1995 | WIPO . |
| WO97/44333 | 11/1997 | WIPO . |
| WO 98/18461 | 5/1998 | WIPO . |
| WO 98/31359 | 7/1998 | WIPO . |
| WO 99/32457 | 7/1999 | WIPO . |
| WO 99/37621 | 7/1999 | WIPO . |

*Primary Examiner*—Bernard Dentz
*Attorney, Agent, or Firm*—Philippe L. Durette; Melvin Winokur; Anthony D. Sabatelli

[57] ABSTRACT

The present invention relates to compounds and derivatives thereof, their synthesis, and their use as integrin receptor antagonists. More particularly, the compounds of the present invention are antagonists of the integrin receptors $\alpha v \beta 3$, $\alpha v \beta 5$ and/or $\alpha v \beta 6$ and are useful for inhibiting bone resorption, treating and preventing osteoporosis, and inhibiting vascular restenosis, diabetic retinopathy, macular degeneration, angiogenesis, atherosclerosis, inflammation, inflammatory arthritis, viral disease, and tumor growth and metastasis.

33 Claims, No Drawings

INTEGRIN RECEPTOR ANTAGONISTS

CROSS-REFERENCE TO RELATED APPLICATIONS

The present invention is related to U.S. Provisional application Ser. No. 60/094,478, filed Jul. 29, 1998, the contents of which are hereby incorporated by reference.

FIELD OF THE INVENTION

The present invention relates to compounds and derivatives thereof, their synthesis, and their use as integrin receptor antagonists. More particularly, the compounds of the present invention are antagonists of the integrin receptors αvβ3, αvβ5 and/or αvβ6 and are useful for inhibiting bone resorption, treating and preventing osteoporosis, and inhibiting vascular restenosis, diabetic retinopathy, macular degeneration, angiogenesis, atherosclerosis, inflammation, inflammatory arthritis, viral disease, tumor growth, and metastasis.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane receptors through which cells attach and communicate with extracellular matrices and other cells. (See S. B. Rodan and G. A. Rodan, "Integrin Function In Osteoclasts," *Journal of Endocrinology*, Vol. 154, S47–S56 (1997), which is incorporated by reference herein in its entirety).

In one aspect of the present invention, the compounds herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin in osteoclasts, e.g., in rat, chicken, mouse and human osteoclasts, is an integrin receptor known as αvβ3, which is thought to interact in bone with matrix proteins that contain the RGD sequence. Antibodies to αvβ3 block bone resorption in vitro indicating that this integrin plays a key role in the resorptive process. There is increasing evidence to suggest that αvβ3 ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, αvβ3 ligands have been found to be useful in treating and/or inhibiting restenosis (i.e. recurrence of stenosis after corrective surgery on the heart valve), atherosclerosis, diabetic retinopathy, macular degeneration, and angiogenesis (i.e. formation of new blood vessels), and inhibiting viral disease. Moreover, it has been postulated that the growth of tumors depends on an adequate blood supply, which in turn is dependent on the growth of new vessels into the tumor; thus, inhibition of angiogenesis can cause tumor regression in animal models (See *Harrison's Principles of Internal Medicine*, 12th ed., 1991, which is incorporated by reference herein in its entirety). Therefore, αvβ3 antagonists which inhibit angiogenesis can be useful in the treatment of cancer by inhibiting tumor growth (See, e.g., Brooks et al., *Cell*, 79:1157–1164 (1994), which is incorporated by reference herein in its entirety).

Evidence has also been presented suggesting that angiogenesis is a central factor in the initiation and persistence of arthritic disease, and that the vascular integrin αvβ3 may be a preferred target in inflammatory arthritis. Therefore, αvβ3 antagonists which inhibit angiogenesis may represent a novel therapeutic approach to the treatment of arthritic disease, such as rheumatoid arthritis (see C. M. Storgard, et al., "Decreased angiogenesis and arthritic disease in rabbits treated with an αvβ3 antagonist," *J. Clin. Invest.*, 103: 47–54 (1999), which is incorporated by reference herein in its entirety).

Moreover, compounds of this invention can also inhibit neovascularization by acting as antagonists of the integrin receptor, αvβ5. A monoclonal antibody for αvβ5 has been shown to inhibit VEGF-induced angiogenesis in rabbit cornea and the chick chorioallantoic membrane model (See M. C. Friedlander, et. al., *Science* 270:1500–1502 (1995), which is incorporated by reference herein in its entirety). Thus, compounds that antagonize αvβ5 are useful for treating and preventing macular degeneration, diabetic retinopathy, tumor growth, and metastasis.

Additionally, compounds of the instant invention can inhibit angiogenesis and inflammation by acting as antagonists of the integrin receptor, αvβ6, which is expressed during the later stages of wound healing and remains expressed until the wound is closed (See Christofidou-Solomidou, et al., "Expression and Function of Endothelial Cell αv Integrin Receptors in Wound-Induced Human Angiogenesis in Human Skin/SCID Mice Chimeras, *American Journal of Pathology*, Vol. 151, No. 4, pp. 975–983 (October 1997), which is incorporated by reference herein in its entirety). It is postulated that αvβ6 plays a role in the remodeling of the vasculature during the later stages of angiogenesis. Also, αvβ6 participates in the modulation of epithelial inflammation and is induced in response to local injury or inflammation (See Xiao-Zhu Huang, et al., "Inactivation of the Integrin β6 Subunit Gene Reveals a Role of Epithelial Integrins in Regulating Inflammation in the Lungs and Skin," *Journal of Cell Biology*, Vol. 133, No.4, pp. 921–928 (May 1996), which is incorporated by reference herein in its entirety). Accordingly, compounds that antagonize αvβ6 are useful in treating or preventing cancer by inhibiting tumor growth and metastasis.

In addition, certain compounds of this invention antagonize both the αvβ3 and αvβ5 receptors. These compounds, referred to as "dual αvβ3/αvβ5 antagonists," are useful for inhibiting bone resorption, treating and preventing osteoporosis, and inhibiting vascular restenosis, diabetic retinopathy, macular degeneration, angiogenesis, atherosclerosis, inflammation, inflammatory arthritis, viral disease, tumor growth, and metastasis.

In addition, certain compounds of this invention are useful as mixed αvβ3, αvβ5, and αvβ6 receptor antagonists.

Peptidyl as well as peptidomimetic antagonists of the αvβ3 integrin receptor have been described both in the scientific and patent literature. For example, reference is made to W. J. Hoekstra and B. L. Poulter, *Curr. Med. Chem.* 5: 195–204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; EP 853084; EP 854140; EP 854145; and U.S. Pat. No. 5,780,426. Evidence of the ability of αvβ3 integrin receptor antagonists to prevent bone resorption in vitro and in vivo has been presented (see V. W. Engleman et al., "A Peptidomimetic Antagonist of the αvβ3 Integrin Inhibits Bone Resorption In Vitro and Prevents Osteoporosis In Vivo," *J. Clin. Invest.* 99: 2284–2292 (1997); S. B. Rodan et al., "A High Affinity Non-Peptide αvβ3 Ligand Inhibits Osteoclast Activity In Vitro and In Vivo," *J. Bone Miner. Res.* 11: S289 (1996); J. F. Gourvest et al., "Prevention of OVX-Induced Bone Loss With a Non-peptidic Ligand of the αvβ3 Vitronectin Receptor," *Bone* 23: S612 (1998); M. W. Lark et al., "An Orally Active Vitronectin Receptor αvβ3 Antagonist Prevents Bone Resorption In Vitro and In Vivo in the Ovariectomized Rat," *Bone* 23: S219 (1998)).

The αvβ3 integrin receptor recognizes the Arg-Gly-Asp (RGD) tripeptide sequence in its cognate matrix and cell surface glycoproteins (see J. Samanen, et al., "vascular Indications for Integrin αv Antagonists," *Curr. Pharmaceut. Design* 3: 545–584(1997)). A benzazepine nucleus has been employed among others by Genentech and SmithKline Beecham as a conformationally constrained Gly-Asp mimetic to elaborate nonpeptide αvβ3 integrin receptor antagonists substituted at the N-terminus with heterocyclic arginine mimetics (see R. M. Keenan et al., "Discovery of Potent Nonpeptide Vitronectin Receptor (αvβ3) Antagonists," *J. Med. Chem.* 40: 2289–2292 (1997); R. M. Keenan et al., "Benzimidazole Derivatives As Arginine Mimetics in 1,4-Benzodiazepine Nonpeptide Vitronectin Receptor (αvβ3) Antagonists," *Bioorg. Med. Chem. Lett.* 8: 3165–3170 (1998); and R. M. Keenan et al., "Discovery of an Imidazopyridine-Containing 1,4-Benzodiazepine Nonpeptide Vitronectin Receptor (αvβ3) Antagonist With Efficacy in a Restenosis Model," *Bioorg. Med. Chem. Lett.* 8: 3171–3176 (1998). Patents assigned to SmithKline Beecham that disclose such benzazepine, as well as related benzodiazepine and benzocycloheptene, αvβ3 integrin receptor antagonists include WO 96/00574, WO 96/00730, WO 96/06087, WO 96/26190, WO 97/24119, WO 97/24122, WO 97/24124, WO 98/15278, WO 99/05107, WO 99/06049, WO 99/15170, and WO 99/15178, and to Genentech include WO 97/34865. The dibenzocycloheptene, as well as dibenzoxazepine, nucleus has also been employed as a Gly-Asp mimetic to afford αvβ3 antagonists (see WO 97/01540, WO 98/30542, WO 99/11626, and WO 99/15508 all assigned to SmithKline Beecham).

However, there still remains a need for small-molecule, non-peptide selective integrin receptor antagonists that display improved potency, pharmacodynamic, and pharmacokinetic properties, such as oral bioavailability and duration of action, over already described compounds. Such compounds would prove to be useful for the treatment, prevention, or suppression of various pathologies enumerated above that are mediated by integrin receptor binding and cell adhesion and activation.

It is therefore an object of the present invention to provide compounds which are useful as integrin receptor antagonists.

It is another object of the present invention to provide compounds which are useful as αvβ3 receptor antagonists.

It is another object of the present invention to provide compounds which are useful as αvβ5 receptor antagonists.

It is another object of the present invention to provide compounds which are useful as αvβ6 receptor antagonists.

It is another object of the present invention to provide compounds which are useful as both αvβ3/αvβ5 receptor antagonists.

It is another obejct of the present invention to provide compounds which are useful as mixed αvβ3, αvβ5 and αvβ6 receptor antagonists.

It is another object of the present invention to provide pharmaceutical compositions comprising integrin receptor antagonists.

It is another object of the present invention to provide methods for making the pharmaceutical compositions of the present invention.

It is another object of the present invention to provide methods for eliciting an integrin receptor antagonizing effect in a mammal in need thereof by administering the compounds and pharmaceutical compositions of the present invention.

It is another object of the present invention to provide compounds and pharmaceutical compositions useful for inhibiting bone resorption, restenosis, atherosclerosis, inflammation, inflammatory arthritis, viral disease, diabetic retinopathy, macular degeneration, angiogenesis, tumor growth and metastasis.

It is another object of the present invention to provide compounds and pharmaceutical compositions useful for treating osteoporosis.

It is another object of the present invention to provide methods for inhibiting bone resorption, restenosis, atherosclerosis, inflammation, inflammatory arthritis, viral disease, diabetic retinopathy, macular degeneration, angiogenesis, tumor growth and metastasis.

It is another object of the present invention to provide methods for treating osteoporosis.

These and other objects will become readily apparent from the detailed description which follows.

SUMMARY OF THE INVENTION

The present invention relates to compounds described by the following chemical formula:

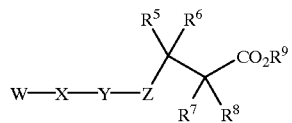

wherein W is selected from the group consisting of
- a 5- or 6-membered monocyclic aromatic or nonaromatic ring system having 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and
- a 9- to 14-membered polycyclic ring system, wherein one or more of the rings is aromatic, and wherein the polycyclic ring system has 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents;

X is selected from the group consisting of
—$(CH_2)_v$—, and
—$(CH_2)_v NR^4 (CH_2)_v$—; wherein any methylene ($CH_2$) carbon atom, other than in $R^4$, is either unsubstituted or substituted with one or two $R^3$ substitutents;

Y is a biarylene ring system comprising 5- or 6-membered aromatic rings, wherein said biarylene ring system comprises 0–6 heteroatoms selected from the group consisting of N, O, and S wherein said biarylene ring system is either unsubstituted or substituted with one or more $R^1$ substituents;

Z is selected from the group consisting of

—$CH_2CH_2$— and —CH=CH—, wherein either carbon atom can be substituted by one or two $R^3$ substituents;

each $R^1$ is independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-S(O)$_p$, $(C_{1-8}$ alkyl$)_p$ aminocarbonyl, $C_{1-8}$ alkyloxycarbonylamino, $(C_{1-8}$ alkyl$)_p$aminocarbonyloxy, (aryl $C_{1-8}$ alkyl$)_p$amino, (aryl$)_p$ amino, aryl $C_{1-8}$ alkylsulfonylamino, and $C_{1-8}$ alkylsulfonylamino;

or two $R^1$ substituents, when on the same carbon atom, are taken together with the carbon atom to which they are attached to form a carbonyl group;

each $R^3$ is independently selected from the group consisting of hydrogen,
aryl,
$C_{1-10}$ alkyl,
aryl—$(CH_2)_r$—O—$(CH_2)_s$—,
aryl—$(CH_2)_r$S(O)$_p$—$(CH_2)_s$—,
aryl—$(CH_2)_r$—C(O)—$(CH_2)_s$—,
aryl—$(CH_2)_r$—C(O)—N($R^4$)—$(CH_2)_s$—,
aryl—$(CH_2)_r$—N($R^4$)—C(O)—$(CH_2)_s$—,
aryl—$(CH_2)_r$N($R^4$)—$(CH_2)_s$—,
halogen,
hydroxyl,
oxo,
trifluoromethyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡—C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino, $C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or two $R^3$ substituents, when on the same carbon atom are taken together with the carbon atom to which they are attached to form a carbonyl group or a cyclopropyl group,
wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;
each $R^4$ is independently selected from the group consisting of
hydrogen,
aryl,
aminocarbonyl,
$C_{3-8}$ cycloalkyl,
amino $C_{1-6}$ alkyl,
(aryl$)_p$aminocarbonyl,
(aryl $C_{1-5}$ alkyl$)_p$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_p$amino $C_{2-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of $R^4$ are either unsubstituted or substituted with one to three $R^1$ substituents;
$R^5$ and $R^6$ are each independently selected from the group consisting of
hydrogen,
$C_{1-10}$ alkyl,
aryl,
aryl—$(CH_2)_r$—O—$(CH_2)_s$,
aryl—$(CH_2)_r$S(O)$_p$—$(CH_2)_s$,
aryl—$(CH_2)_r$—C(O)—$(CH_2)_s$,
aryl—$(CH_2)_r$—C(O)—N($R^4$)—$(CH_2)_s$,
aryl—$(CH_2)_r$—N($R^4$)—C(O)—$(CH_2)_s$,
aryl—$(CH_2)_r$N($R^4$)—$(CH_2)_s$,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—, $C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl;
or $R^5$ and $R^6$ are taken together with the carbon atom to which they are attached to form a carbonyl group,
wherein any of the alkyl groups of $R^5$ or $R^6$ are either unsubstituted or substituted with one to three $R^1$ substituents,
and provided that each $R^5$ and $R^6$ are selected such that in the resultant compound the carbon atom to which $R^5$ and $R^6$ are attached is itself attached to no more than one heteroatom;

$R^7$ and $R^8$ are each independently selected from the group consisting of
hydrogen,
$C_{1-10}$ alkyl,
aryl,
aryl—$(CH_2)_r$—O—$(CH_2)_s$,
aryl—$(CH_2)_r$S(O)$_p$—$(CH_2)_s$,
aryl—$(CH_2)_r$—C(O)—$(CH_2)_s$—,
aryl—$(CH_2)_r$—C(O)—N($R^4$)—$(CH_2)_s$,
aryl—$(CH_2)_r$—N($R^4$)—C(O)—$(CH_2)_s$—,
aryl—$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy, aryl $C_{1-6}$ alkyl,
$(C_{1-6}$ alkyl$)_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
arylaminocarbonylamino,
$(C_{1-8}$ alkyl$)_p$aminocarbonylamino,
$(C_{1-8}$ alkyl$)_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl,
(aryl $C_{1-8}$ alkyl)$_p$aminocarbonyl $C_{1-6}$ alkyl, and
$C_{7-20}$ polycyclyl $C_{0-8}$ alkylsulfonylamino,
wherein any of the alkyl groups of $R^7$ and $R^8$ are either unsubstituted or substituted with one to three $R^1$ substituents,
and provided that each $R^7$ and $R^8$ are selected such that in the resultant compound the carbon atom to which $R^7$ and $R^8$ are attached is itself attached to no more than one heteroatom;
$R^9$ is selected from the group consisting of hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;
wherein each p is independently an integer from 0 to 2;
each r is independently an integer from 1 to 3;
each s is independently an integer from 0 to 3;
each t is independently an integer from 0 to 3; and
each v is independently an integer from 0 to 6;
and the pharmaceutically acceptable salts thereof.

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an integrin receptor antagonizing effect in a mammal in need thereof by administering the compounds and pharmaceutical compositions of the present invention.

The present invention also relates to methods for inhibiting bone resorption, restenosis, atherosclerosis, inflammation, inflammatory arthritis, viral disease, diabetic retinopathy, macular degeneration, angiogenesis, and tumor growth and metastasis by administering the compounds and pharmaceutical compositions of the present invention.

The present invention also relates to methods for treating osteoporosis by administering the compounds and pharmaceutical compositions of the present invention.

DETAILED DESCRIPTION OF THE INVENTION

The present invention relates to compounds useful as integrin receptor antagonists. Compounds of the present invention are described by the following chemical formula:

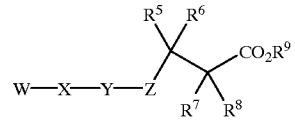

wherein W is selected from the group consisting of
a 5- or 6-membered monocyclic aromatic or nonaromatic ring system having 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and
a 9- to 14-membered polycyclic ring system, wherein one or more of the rings is aromatic, and wherein the polycyclic ring system has 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents;

X is selected from the group consisting of
—$(CH_2)_v$—, and
—$(CH_2)_v NR^4 (CH_2)_v$—; wherein any methylene ($CH_2$) carbon atom, other than in $R^4$, is either unsubstituted or substituted with one or two $R^3$ substitutents;

Y is a biarylene ring system comprising 5- or 6-membered aromatic rings, wherein said biarylene system comprises 0–6 heteroatoms selected from the group consisting of N, O, and S wherein said biarylene ring system is either unsubstituted or substituted with one or more $R^1$ substituents;

Z is selected from the group consisting of

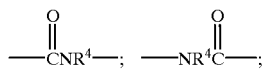

—$CH_2CH_2$— and —CH═CH—, wherein either carbon atom can be substituted by one or two $R^3$ substituents;

each $R^1$ is independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-S(O)$_p$, $(C_{1-8}$ alkyl$)_p$aminocarbonyl, $C_{1-8}$ alkyloxycarbonylamino, $(C_{1-8}$ alkyl$)_p$ aminocarbonyloxy, (aryl $C_{1-8}$ alkyl)$_p$amino, (aryl)$_p$ amino, aryl $C_{1-8}$ alkylsulfonylamino, and $C_{1-8}$ alkylsulfonylamino;

or two $R^1$ substituents, when on the same carbon atom, are taken together with the carbon atom to which they are attached to form a carbonyl group;

each $R^3$ is independently selected from the group consisting of
hydrogen,
aryl,
$C_{1-10}$ alkyl,
aryl—$(CH_2)_r$—O—$(CH_2)_s$,
aryl—$(CH_2)_r S(O)_p$—$(CH_2)_s$,
aryl—$(CH_2)_r$—C(O)—$(CH_2)_s$,
aryl—$(CH_2)_r$—C(O)—N($R^4$)—$(CH_2)_s$,
aryl—$(CH_2)_r$—N($R^4$)—C(O)—$(CH_2)_s$—,
aryl—$(CH_2)_r$—N($R^4$)—$(CH_2)_s$,
halogen,
hydroxyl,
oxo,
trifluoromethyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$═CH—$(CH_2)_t$—,
$C_{1-6}$ alkyl—CH═CH—$(CH_2)_t$—,
$C_{3-7}$ cycloalkyl—CH═CH—$(CH_2)_t$—,
aryl—CH═CH—$(CH_2)_t$—,
$C_{1-6}$ alkylaryl—CH═CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
$(C_{1-8}$ alkyl$)_p$aminosulfonylamino, ($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl;

or two $R^3$ substituents, when on the same carbon atom are taken together with the carbon atom to which they are attached to form a carbonyl group or a cyclopropyl group, wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;

each $R^4$ is independently selected from the group consisting of
hydrogen,
aryl,
aminocarbonyl,
$C_{3-8}$ cycloalkyl,
amino $C_{1-6}$ alkyl,
(aryl)$_p$aminocarbonyl,
(aryl $C_{1-5}$ alkyl)$_p$aminocarbonyl,
hydroxycarbonyl $C_{1-6}$ alkyl,
$C_{1-8}$ alkyl,
aryl $C_{1-6}$ alkyl,
($C_{1-6}$ alkyl)$_p$amino $C_{2-6}$ alkyl,
(aryl $C_{1-6}$ alkyl)$_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
($C_{1-8}$ alkyl)$_p$aminocarbonyl,
aminosulfonyl,
$C_{1-8}$ alkylaminosulfonyl,
(aryl)$_p$aminosulfonyl,
(aryl $C_{1-8}$ alkyl)$_p$aminosulfonyl,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl, wherein any of the alkyl groups of $R^4$ are either unsubstituted or substituted with one to three $R^1$ substituents;

$R^5$ and $R^6$ are each independently selected from the group consisting of
hydrogen,
$C_{1-10}$ alkyl,
aryl,
aryl—$(CH_2)_r$—O—$(CH_2)_s$,
aryl—$(CH_2)_r$S(O)$_p$—$(CH_2)_s$,
aryl—$(CH_2)_r$—C(O)—$(CH_2)_s$,
aryl—$(CH_2)_r$—C(O)—N($R^4$)—$(CH_2)_s$,
aryl—$(CH_2)_r$—N($R^4$)—C(O)—$(CH_2)_s$,
aryl—$(CH_2)_r$N($R^4$)—$(CH_2)_s$,
halogen,
hydroxyl,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
$C_{3-8}$ cycloalkyl,
($C_{1-6}$ alkyl)$_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡—C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy,
aryl $C_{1-6}$ alkyl,
($C_{1-6}$ alkyl)$_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy, $C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or $R^5$ and $R^6$ are taken together with the carbon atom to which they are attached to form a carbonyl group,
wherein any of the alkyl groups of $R^5$ or $R^6$ are either unsubstituted or substituted with one to three $R^1$ substituents,
and provided that each $R^5$ and $R^6$ are selected such that in the resultant compound the carbon atom to which $R^5$ and $R^6$ are attached is itself attached to no more than one heteroatom;

$R^7$ and $R^8$ are each independently selected from the group consisting of hydrogen,
$C_{1-10}$ alkyl,
aryl,
aryl—$(CH_2)_r$—O—$(CH_2)_s$,
aryl—$(CH_2)_r$S(O)$_p$—$(CH_2)_s$,
aryl—$(CH_2)_r$—C(O)—$(CH_2)_s$,
aryl—$(CH_2)_r$—C(O)—N(R$^4$)—$(CH_2)_s$,
aryl—$(CH_2)_r$—N(R$^4$)—C(O)—$(CH_2)_s$,
aryl—$(CH_2)_r$—N(R$^4$)—$(CH_2)_s$,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—SO$_2$—$(CH_2)_t$—,
$C_{1-6}$ alkylaryl—SO$_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino, C<sub>1-8</sub> alkoxycarbonylamino C<sub>1-8</sub> alkyl,
aryloxycarbonylamino C<sub>1-8</sub> alkyl,
aryl C<sub>1-8</sub> alkoxycarbonylamino,
aryl C<sub>1-8</sub> alkoxycarbonylamino C<sub>1-8</sub> alkyl,
C<sub>1-8</sub> alkylcarbonylamino C<sub>1-6</sub> alkyl,
arylcarbonylamino C<sub>1-6</sub> alkyl,
aryl C<sub>1-6</sub> alkylcarbonylamino,
aryl C<sub>1-6</sub> alkylcarbonylamino C<sub>1-6</sub> alkyl,
aminocarbonylamino C<sub>1-6</sub> alkyl,
arylaminocarbonylamino,
(C<sub>1-8</sub> alkyl)$_p$aminocarbonylamino,
(C<sub>1-8</sub> alkyl)aminocarbonylamino C<sub>1-6</sub> alkyl,
(aryl)$_p$aminocarbonylamino C<sub>1-6</sub> alkyl,
((aryl C<sub>1-8</sub> alkyl)$_p$aminocarbonyl amino ,
(aryl C<sub>1-8</sub> alkyl)$_p$aminocarbonylamino C<sub>1-6</sub> alkyl,
aminosulfonylamino C<sub>1-6</sub> alkyl,
(C<sub>1-8</sub> alkyl)$_p$aminosulfonylamino,
(C<sub>1-8</sub> alkyl)$_p$aminosulfonylamino C<sub>1-6</sub> alkyl,
(aryl)$_p$aminosulfonylamino C<sub>1-6</sub> alkyl,
(aryl C<sub>1-8</sub> alkyl)$_p$aminosulfonylamino,
(aryl C<sub>1-8</sub> alkyl)$_p$aminosulfonylamino C<sub>1-6</sub> alkyl,
C<sub>1-6</sub> alkylsulfonyl,
C<sub>1-6</sub> alkylsulfonyl C<sub>1-6</sub> alkyl,
arylsulfonyl C<sub>1-6</sub> alkyl,
aryl C<sub>1-6</sub> alkylsulfonyl,
aryl C<sub>1-6</sub> alkylsulfonyl C<sub>1-6</sub> alkyl,
C<sub>1-6</sub> alkylcarbonyl,
C<sub>1-6</sub> alkylcarbonyl C<sub>1-6</sub> alkyl,
arylcarbonyl C<sub>1-6</sub> alkyl,
aryl C<sub>1-6</sub> alkylcarbonyl,
aryl C<sub>1-6</sub> alkylcarbonyl C<sub>1-6</sub> alkyl,
C<sub>1-6</sub> alkylthiocarbonylamino,
C<sub>1-6</sub> alkylthiocarbonylamino C<sub>1-6</sub> alkyl,
arylthiocarbonylamino C<sub>1-6</sub> alkyl,
aryl C<sub>1-6</sub> alkylthiocarbonylamino,
aryl C<sub>1-6</sub> alkylthiocarbonylamino C<sub>1-6</sub> alkyl,
(C<sub>1-8</sub> alkyl)$_p$aminocarbonyl C<sub>1-6</sub> alkyl,
(aryl)$_p$aminocarbonyl C<sub>1-6</sub> alkyl,
(aryl C<sub>1-8</sub> alkyl)$_p$aminocarbonyl,
(aryl C<sub>1-8</sub> alkyl)$_p$aminocarbonyl C<sub>1-6</sub> alkyl, and
C<sub>7-20</sub> polycyclyl C<sub>0-8</sub> alkylsulfonylamino,
wherein any of the alkyl groups of R$^7$ and R$^8$ are either unsubstituted or substituted with one to three R$^1$ substituents,
and provided that each R$^7$ and R$^8$ are selected such that in the resultant compound the carbon atom to which R$^7$ and R$^8$ are attached is itself attached to no more than one heteroatom;
R$^9$ is selected from the group consisting of
hydrogen,
C<sub>1-8</sub> alkyl,
aryl,
aryl C<sub>1-8</sub> alkyl,
C<sub>1-8</sub> alkylcarbonyloxy C<sub>1-4</sub> alkyl,
aryl C<sub>1-8</sub> alkylcarbonyloxy C<sub>1-4</sub> alkyl,
C<sub>1-8</sub> alkylaminocarbonylmethylene, and
C<sub>1-8</sub> dialkylaminocarbonylmethylene;
wherein each p is independently an integer from 0 to 2;

each r is independently an integer from 1 to 3;
each s is independently an integer from 0 to 3;
each t is independently an integer from 0 to 3; and
each v is independently an integer from 0 to 6;
and the pharmaceutically acceptable salts thereof.

In the compounds of the present invention, W is preferably selected from the group consisting of

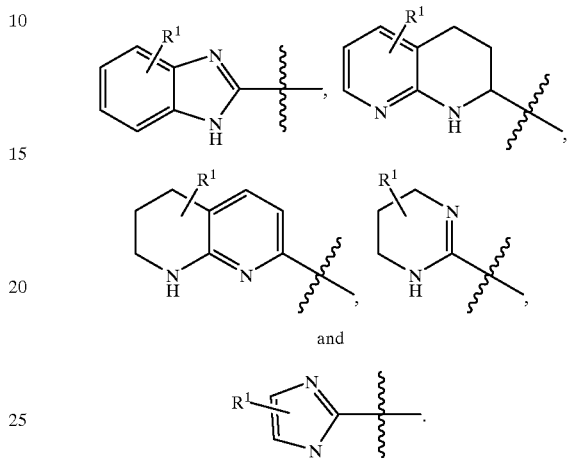

and

More preferably, W is selected from the group consisting of

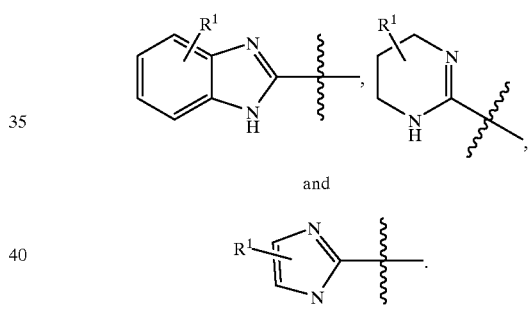

and

Most preferably, W is selected from the group consisting of

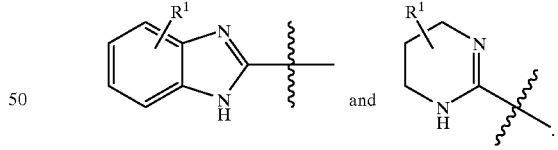

In the compounds of the present invention, Y is preferably selected from the group consisting of

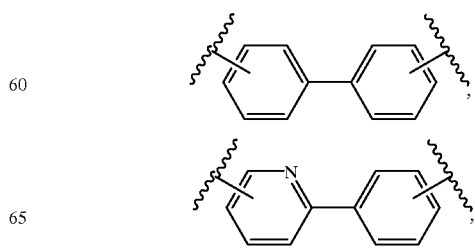

-continued

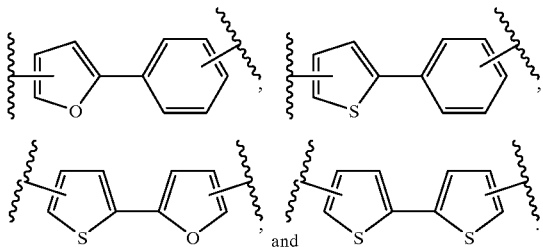
, and

More preferably, Y is

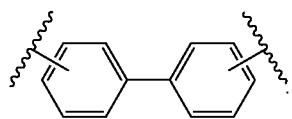

Most preferably, Y is

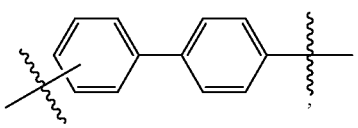

such that the X moiety is attached at the variable position and the Z moiety is attached at the para position. In other words, in these preferred embodiments for Y, the X and Z substituents have the following orientation with respect to the biarylene moiety

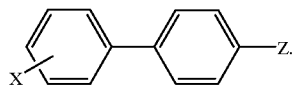

In the compounds of the present invention, Z is preferably selected from the group consisting of

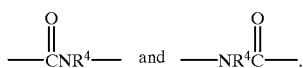

More preferably, Z is

In the compounds of the present invention, $R^1$ is preferably selected from the group consisting of hydrogen, halogen, $C_{1-10}$ alkyl, $C_{3-8}$ cycloalkyl, $C_{3-8}$ cycloheteroalkyl, hydroxy, nitro, cyano, trifluoromethyl, and trifluoromethoxy.

More preferably, $R^1$ is selected from the group consisting of hydrogen, halogen, $C_{1-10}$ alkyl, $C_{3-8}$ cycloalkyl, trifluoromethyl, and trifluoromethoxy.

In the compounds of the present invention, $R^3$ is preferably selected from the group consisting of
hydrogen,
fluoro,
trifluoromethyl,
aryl,
$C_{1-8}$ alkyl,
aryl$C_{1-6}$ alkyl
hydroxyl,
oxo,
arylaminocarbonyl,
aryl $C_{1-5}$ alkylaminocarbonyl,
aminocarbonyl, and
aminocarbonyl $C_{1-6}$ alkyl.

More preferably, $R^3$ is selected from the group consisting of
fluoro,
aryl,
$C_{1-8}$ alkyl,
aryl$C_{1-6}$ alkyl
hydroxyl,
oxo, and
arylaminocarbonyl.

In the compounds of the present invention, $R^4$ is preferably selected from the group consisting of hydrogen,
aryl,
$C_{3-8}$ cycloalkyl,
$C_{1-8}$ alkyl,
$C_{1-8}$ alkylcarbonyl,
arylcarbonyl,
$C_{1-6}$ alkylsulfonyl,
arylsulfonyl,
aryl$C_{1-6}$alkylsulfonyl,
aryl$C_{1-6}$alkylcarbonyl,
$C_{1-8}$alkylaminocarbonyl,
aryl$C_{1-5}$alkylaminocarbonyl,
aryl$C_{1-8}$alkoxycarbonyl, and
$C_{1-8}$alkoxycarbonyl.

More preferably, $R^4$ is selected from the group consisting of hydrogen,
$C_{1-8}$ alkyl,
$C_{1-8}$ alkylcarbonyl,
arylcarbonyl,
aryl$C_{1-6}$alkylcarbonyl,
$C_{1-6}$ alkylsulfonyl,
arylsulfonyl, and
aryl$C_{1-6}$alkylsulfonyl.

In one embodiment of the present invention, $R^5$ and $R^6$ are each independently selected from the group consisting of
hydrogen,
aryl,
$C_{1-8}$ alkyl,
aryl—C≡C—$(CH_2)_t$—,
aryl $C_{1-6}$ alkyl,
$CH_2$=CH—$(CH_2)_t$—, and
HC≡C—$(CH_2)_t$.

In a class of this embodiment of the present invention, $R^6$ is hydrogen and $R^5$ is selected from the group consisting of
hydrogen,
aryl,
$C_{1-8}$ alkyl,
aryl—C≡C—$(CH_2)_t$—,
aryl $C_{1-6}$ alkyl, CH$_2$=CH—(CH$_2$)$_t$—, and
HC≡C—(CH$_2$)$_t$—.
In a subclass of this class of the present invention, R$^6$, R$^7$, and R$^8$ are each hydrogen and R$^5$ is selected from the group consisting of
hydrogen,
aryl,
C$_{1-8}$ alkyl,
aryl—C≡C—(CH$_2$)$_t$—,
aryl C$_{1-6}$ alkyl,
CH$_2$=CH—(CH$_2$)$_t$—, and
HC≡C—(CH$_2$)$_t$—.

In another embodiment of the present invention, R$^7$ and R$^8$ are each independently selected from the group consisting of
hydrogen,
aryl,
C$_{1-8}$ alkylcarbonylamino,
C$_{1-8}$ alkylsulfonylamino,
arylcarbonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonylamino C$_{1-6}$ alkyl,
arylaminocarbonylamino,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl, and
C$_{7-20}$ polycyclyl C$_{0-8}$ alkylsulfonylamino.

In a class of this embodiment of the present invention, R$^8$ is hydrogen and R$^7$ is selected from the group consisting of
hydrogen,
aryl,
C$_{1-8}$ alkylcarbonylamino,
aryl C$_{1-6}$ alkylcarbonylamino,
arylcarbonylamino,
C$_{1-8}$ alkylsulfonylamino,
aryl C$_{1-6}$ alkylsulfonylamino,
arylsulfonylamino,
C$_{1-8}$ alkoxycarbonylamino,
aryl C$_{1-8}$ alkoxycarbonylamino,
arylaminocarbonylamino,
(C$_{1-8}$ alkyl)$_p$aminocarbonylamino,
(aryl C$_{1-8}$ alkyl)$_p$aminocarbonylamino,
(C$_{1-8}$ alkyl)$_p$aminosulfonylamino, and
(aryl C$_{1-8}$ alkyl)$_p$aminosulfonylamino.

In a subclass of this class of the present invention, R$^5$, R$^6$, and R$^8$ are each hydrogen and R$^7$ is selected from the group consisting of
hydrogen,
aryl,
C$_{1-8}$ alkylcarbonylamino,
aryl C$_{1-6}$ alkylcarbonylamino,
arylcarbonylamino,
C$_{1-8}$ alkylsulfonylamino,
aryl C$_{1-6}$ alkylsulfonylamino,
arylsulfonylamino,
C$_{1-8}$ alkoxycarbonylamino,
aryl C$_{1-8}$ alkoxycarbonylamino,
arylaminocarbonylamino,
(C$_{1-8}$ alkyl)$_p$aminocarbonylamino,
(aryl C$_{1-8}$ alkyl)$_p$aminocarbonylamino,
(C$_{1-8}$ alkyl)$_p$aminosulfonylamino, and
(aryl C$_{1-8}$ alkyl)$_p$aminosulfonylamino.

In the compounds of the present invention, R$^9$ is preferably selected from the group consisting of hydrogen, methyl, and ethyl.

More preferably, R$^9$ is hydrogen.

Preferably, in the compounds of the present invention, each v is independently an integer from 0 to 2.

Illustrative but nonlimiting examples of compounds of the present invention that are useful as integrin receptor antagonists are the following:

3'-[N-(3,4,5,6-tetrahydropyrimidin-2-yl)amino]biphenyl-4-carbonyl-2(S)-phenylsulfonylamino-β-alanine, 3'-[N-(5,6,7,8-tetrahydro-[1,8]napthyridin-2-yl)amino]biphenyl-4-carbonyl-2(S)-phenylsulfonylamino-β-alanine, 2(S)-phenylsulfonylamino-3-{4-[4-(1,4,5,6-tetrahydropyrimidin-2-ylamino)-thiophen-2-yl]-benzoylamino}-propionic acid, 2(S)-phenylsulfonylamino-3-({5-[3-(1H-benzoimidazol-2-ylamino)-phenyl]-pyridine-2-carbonyl}-amino)-propionic acid, 2(S)-phenylsulfonylamino-3-{4-[4-(1,4,5,6-tetrahydropyrimidin-2-ylamino)-furan-2-yl]-benzoylamino}-propionic acid, 2(S)-phenylsulfonylamino-3-{[4'-(1H-imidazol-2-ylamino)-[2,2']bithiophenyl-5-carbonyl]-amino}-propionic acid, 2(S)-phenylsulfonylamino-3-({4-[3-(1H-benzoimidazol-2-ylamino)-phenyl]-1H-pyrazole-3-carbonyl}-amino)-propionic acid, 2(S)-phenylsulfonylamino-3-({5-[5-(1,4,5,6-tetrahydropyrimidin-2-ylamino)-thiophen-2-yl]-furan-2-carbonyl}-amino)-propionic acid, and 3'-[N-pyrimidin-2-yl-amino]biphenyl-4-carbonyl-2(S)-phenylsulfonylamino-propionic acid;
and the pharmaceutically acceptable salts thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention can have chiral centers and can thus occur as racemates, racemic mixtures, single enantiomers, diastereomeric mixtures, and individual diastereomers, with all isomeric forms being included in the present invention. Therefore, where a compound is chiral, the separate enantiomers or diastereomers, substantially free of the other, are included within the scope of the invention; further included are all mixtures of the two enantiomers.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form, known as keto-enol tautomers. The individual tautomers as well as mixtures thereof are encompassed within the compounds of the present invention.

Compounds of the present invention may be separated into diastereoisomeric pairs of enantiomers by, for example, fractional crystallization from a suitable solvent, for example, methanol or ethyl acetate or a mixture thereof. The pair of enantiomers thus obtained may be separated into individual stereoisomers by conventional means, for example, by the use of an optically active acid as a resolving agent, or by HPLC using a chiral stationary phase. Alternatively, any enantiomer of a compound of the present invention may be obtained by stereospecific synthesis using optically pure starting materials or reagents of known configuration.

Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "integrin receptor antagonist," as used herein, refers to a compound which binds to and antagonizes either the $\alpha v\beta 3$ receptor, the $\alpha v\beta 5$ receptor, or the $\alpha v\beta 6$ receptor, or a compound which binds to and antagonizes combinations of these receptors (for example, a dual $\alpha v\beta 3/\alpha v\beta 5$ receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O, or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or polycyclic system comprising at least one aromatic ring, wherein the monocylic or polycyclic system contains 0, 1, 2, 3, or 4 heteroatoms chosen from N, O, or S, and wherein the monocylic or polycylic system is either unsubstituted or substituted with one or more groups independently selected from hydrogen, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylamino, $C_{1-6}$ alkylamino $C_{1-6}$ alkyl, di($C_{1-6}$) alkylamino, di($C_{1-6}$) alkylamino-$C_{1-6}$ alkyl, $C_14$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrrolyl, pyrazolyl, pyrazinyl, pyrimidinyl, imidazolyl, benzimidazolyl, benzthiazolyl, benzoxazolyl, indolyl, thienyl, furyl, dihydrobenzofuryl, benzo(1,3)dioxolanyl, benzo(1,4) dioxanyl, oxazolyl, isoxazolyl, thiazolyl, and isothiazolyl, which are either unsubstituted or substituted with one or more groups independently selected from hydrogen, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylamino, $C_{1-6}$ alkylamino $C_{1-6}$ alkyl, di($C_{1-6}$) alkylamino, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Preferably, the aryl group is unsubstituted, mono-, di-, tri- substituted with one to three of the above-named substituents; more preferably, the aryl group is unsubstituted, mono- or di-substituted with one to two of the above-named substituents.

The term "biarylene" as used herein refers to a nonfused (as opposed to a fused), bicyclic ring system. The biarylene system is incorporated into the molecules of the present invention through two connectivity or bonding points.

The biarylene system comprises two aromatic ring systems, wherein each of the aromatic ring systems is a 5- or 6-membered aromatic ring system. The biarylene system comprises 0–6 heteroatoms selected from the broup consisting of N, O, and S. The biarylene system can be either unsubstituted or substituted with one or more $R^1$ substituents. The two aromatic ring systems of the biarylene system can be the same or different. Nonlimiting examples of biarylene systems useful herein include those selected from the group consisting of

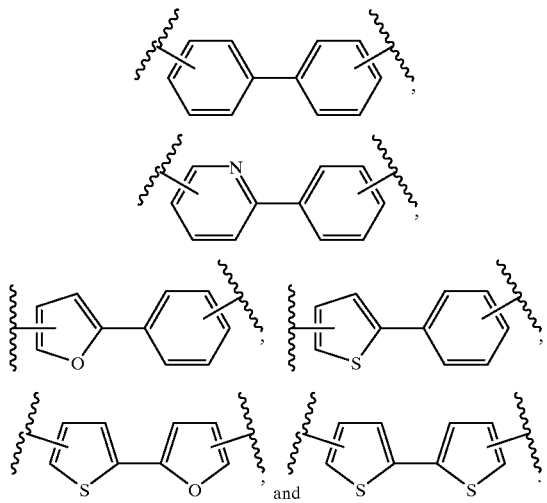

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{1-8}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

In the compounds of the present invention, two $R^2$ substituents, when on the same carbon atom, can be taken together with the carbon atom to which they are attached to form a carbonyl group.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

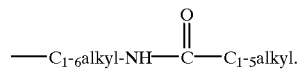

In choosing compounds of the present invention, one of ordinary skill in the art will recognize that the various substituents, i.e. W, X, Y, Z, $R^1$, $R^2$, $R^3$, $R^4$, $R^5$, $R^6$, $R^7$, $R^8$, and $R^9$ are to be chosen in conformity with well-known principles of chemical structure connectivity.

Representative compounds of the present invention typically display submicromolar affinity for the integrin receptors, particularly the αvβ3, αvβ5, and/or αvβ6 receptors. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis.

Illustrating the invention is the method wherein the integrin receptor antagonizing effect is an αvβ3 antagonizing effect. More particularly, the αvβ3 antagonizing effect is selected from inhibition of: bone resorption, restenosis, angiogenesis, diabetic retinopathy, macular degeneration, inflammation, inflammatory arthritis, viral disease, tumor growth, or metastasis. In one embodiment of the method, the αvβ3 antagonizing effect is the inhibition of bone resorption.

Another example of the invention is the method wherein the integrin receptor antagonizing effect is an αvβ5 antagonizing effect. More specifically, the αvβ5 antagonizing effect is selected from inhibition of restenosis, angiogenesis, diabetic retinopathy, macular degeneration, inflammation, tumor growth, or metastasis.

Further illustrating the invention is the method wherein the integrin receptor antagonizing effect is a dual αvβ3/αvβ5 antagonizing effect. More particularly, the dual αvβ3/αvβ5 antagonizing effect is selected from inhibition of: bone resorption, restenosis, angiogenesis, diabetic retinopathy, macular degeneration, inflammation, viral disease, tumor growth, or metastasis.

Even further illustrating the invention is the method wherein the integrin receptor antagonizing effect is an αvβ6 antagonizing effect. More particularly, the αvβ6 antagonizing effect is selected from inhibition of angiogenesis, inflammatory response, or wound healing.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of an integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammation, inflammatory arthritis, viral disease, cancer, tumor growth, and metastasis. More preferably, the condition is selected from osteoporosis and cancer. Most preferably, the condition is osteoporosis.

More specifically exemplifying the invention is a method of eliciting an integrin antagonizing effect in a mammal in need thereof, comprising administering to the mammal a therapeutically effective amount of any of the compounds or any of the pharmaceutical compositions described above. Preferably, the integrin antagonizing effect is an αvβ3 antagonizing effect; more specifically the αvβ3 antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation, inhibition of inflammatory arthritis, inhibition of viral disease, or inhibition of tumor growth or metastasis. Most preferably, the αvβ3 antagonizing effect is inhibition of bone resorption. Alternatively, the integrin antagonizing effect is an αvβ5 antagonizing effect, an αvβ6 antagonizing effect, or a mixed αvβ3, αvβ5, and αvβ6 antagonizing effect. Examples of αvβ5 antagonizing effects are inhibition of restenosis, atherosclerosis, angiogenesis, diabetic retinopathy, macular degeneration, inflammation, or tumor growth. Examples of αvβ6 antagonizing effects are inhibition of angiogenesis, inflammatory response, and wound healing.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions decribed above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization- induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone resorption, tumor growth, cancer, restenosis, atherosclerosis, diabetic retinopathy, macular degeneration, inflammation, inflammatory arthritis, viral disease, and/or angiogenesis.

Also exemplifying the invention are compositions of the integrin antagonists further comprising an active ingredient selected from the group consisting of
a) an organic bisphosphonate or a pharmaceutically acceptable salt or ester thereof,
b) an estrogen receptor modulator,
c) a cytotoxic/antiproliferative agent,
d) a matrix metalloproteinase inhibitor,
e) an inhibitor of epidermal-derived, fibroblast-derived, or platelet-derived growth factors,
f) an inhibitor of VEGF,
g) an inhibitor of Flk-1/KDR, Flt-1, Tck/Tie-2, or Tie-1,
h) a cathepsin K inhibitor,
i) an inhibitor of osteoclast proton ATPase, and
j) a prenylation inhibitor, such as a farnesyl transferase inhibitor or a geranylgeranyl transferase inhibitor or a dual farnesyl/geranylgeranyl transferase inhibitor; and mixtures thereof. (See B. Millauer et al., "Dominant-Negative Inhibition of Flk-1 Suppresses the Growth of Many Tumor Types in Vivo", *Cancer Research* 56, 1615–1620 (1996), which is incorporated by reference herein in its entirety).

Preferably, the active ingredient is selected from the group consisting of:
a) an organic bisphosphonate or a pharmaceutically acceptable salt or ester thereof,
b) an estrogen receptor modulator,
c) an inhibitor of osteoclast proton ATPase, and
d) a cathepsin K inhibitor; and mixtures thereof.

Nonlimiting examples of such bisphosphonates include alendronate, etidronate, pamidronate, risedronate, ibandronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases (see C. Farina et al., "Selective inhibitors of the osteoclast vacuolar proton ATPase as novel bone antiresorptive agents," DDT, 4: 163–172 (1999)).

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, a cathepsin K inhibitor, or an inhibitor of the osteoclast proton ATPase.

Additional illustrations of the invention are methods of treating tumor growth or metastasis in a mammal in need thereof, comprising administering to the mammal a therapeutically effective amount of a compound described above and one or more agents known to be cytotoxic/antiproliferative. Also, the compounds of the present invention can be administered in combination with radiation therapy for treating tumor growth and metastasis.

In addition, the integrin $\alpha v\beta 3$ antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid-induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an $\alpha v\beta 3$ receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an $\alpha v\beta 3$ antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the Schemes and Examples below, various reagent symbols and abbreviations have the following meanings:

| | |
|---|---|
| AcOH: | Acetic acid. |
| BH$_3$.DMS: | Borane.dimethylsulfide. |
| BOC(Boc): | t-Butyloxycarbonyl. |
| BOP: | Benzotriazol-1-yloxytris(dimethylamino)-phosphonium hexafluorophosphate. |
| CBZ(Cbz): | Carbobenzyloxy or benzyloxycarbonyl. |
| CDI: | Carbonyldiimidazole. |
| CH$_2$Cl$_2$: | Methylene chloride. |
| CH$_3$CN | Acetonitrile |
| CHCl$_3$: | Chloroform. |
| DEAD: | Diethyl azodicarboxylate. |
| DIAD: | Diisopropyl azodicarboxylate. |
| DIBAH or DIBAL-H: | Diisobutylaluminum hydride. |
| DIPEA: | Diisopropylethylamine. |
| DMAP: | 4-Dimethylaminopyridine. |
| DME: | 1,2-Dimethoxyethane. |
| DMF: | Dimethylformamide. |
| DMSO: | Dimethylsulfoxide. |
| DPFN: | 3,5-Dimethyl-1-pyrazolylformamidine nitrate. |
| EDC: | 1-(3-Dimethylaminopropyl)-3-ethylcarbodiimide.HCl |
| EtOAc: | Ethyl acetate. |
| EtOH: | Ethanol. |
| HOAc: | Acetic acid. |
| HOAT: | 1-Hydroxy-7-azabenzotriazole |
| HOBT: | 1-Hydroxybenzotriazole. |
| HPLC: | High-performance liquid chromatography. |
| IBCF: | Isobutylchoroformate |

-continued

| | |
|---|---|
| LDA: | Lithium diisopropylamide. |
| MeOH: | Methanol. |
| MNNG | 1,1-methyl-3-nitro-1-nitrosoguanidine |
| NEt$_3$: | Triethylamine. |
| NMM: | N-methylmorpholine. |
| PCA.HCl: | Pyrazole carboxamidine hydrochloride. |
| Pd/C: | Palladiumon activated carbon catalyst. |
| Ph: | Phenyl. |
| PyCLU: | Chloro-N,N,N',N'-(tetramethylene)-formamidinium hexafluorophosphate. |
| pTSA | p-Toluenesulfonic acid. |
| TEA: | Triethylamine. |
| TFA: | Trifluoroacetic acid. |
| THF: | Tetrahydrofuran. |
| TLC: | Thin Layer Chromatography. |
| TMEDA: | N,N,N',N'-Tetramethylenediamine. |
| TMS: | Trimethylsilyl. |

The novel compounds of the present invention can be prepared according to the procedure of the following Schemes and Examples, using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making representative compounds of the present invention. Moreover, by utilizing the procedures described in detail in PCT International Application Publication Nos. WO95/32710, published Dec. 1995, and WO95/17397, published Jun. 29, 1995, both of which are incorporated by reference herein in their entirety, in conjunction with the disclosure contained herein, one of ordinary skill in the art can readily prepare additional compounds of the present invention claimed herein. Additionally, for a general review describing the synthesis of β-alanines which can be utilized as the C-terminus of the compounds of the present invention, see Cole, D. C., *Recent Stereoselective Synthetic Approaces to β-Amino Acids, Tetrahedron*, 1994, 50, 9517–9582; Juaristi, E, et al., *Enantioselective Synthesis of β-Amino Acids, Aldrichimica Acta*, 1994, 27, 3. In particular, synthesis of the 3-methyl-β-alanine is taught in Duggan, M. F. et al., *J. Med. Chem.*, 1995, 38, 3332–3341; the 3-ethynyl-β-alanine is taught in Zablocki, J. A., et al., *J. Med. Chem.*, 1995, 38, 2378–2394; the 3-(pyridin-3-yl)-β-alanine is taught in Rico, J. G. et al., *J. Org. Chem.*, 1993, 58, 7948–7951; and the 2-amino- and 2-tosylamino-β-alanines are taught in Xue, C-B, et al., *Biorg. Med. Chem. Letts.*, 1996, 6, 339–344. The references described in this paragraph are all also incorporated by reference herein in their entirety.

SCHEME 1

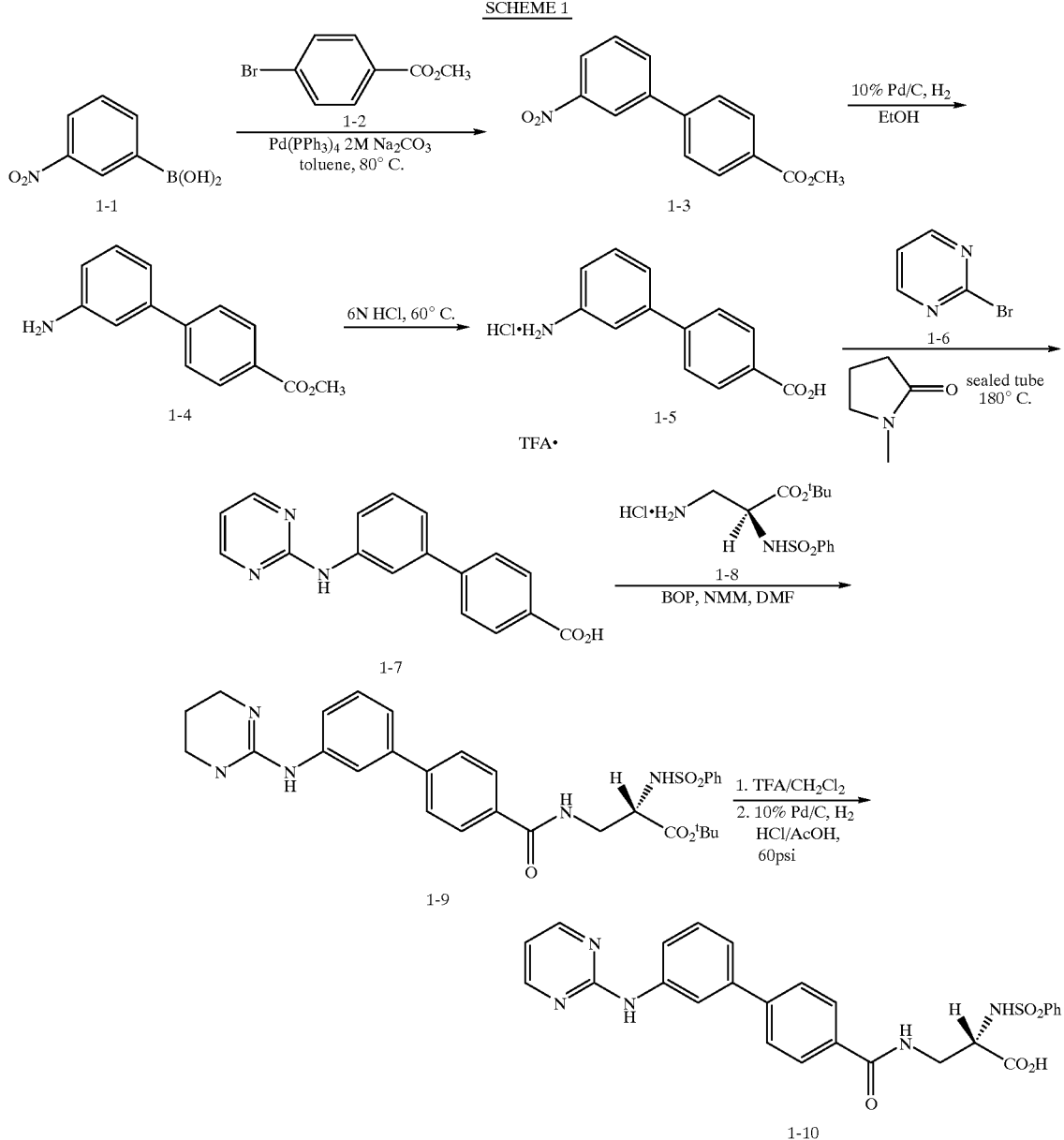

3'-Nitro-biphenyl-4-carboxylic acid methyl ester (1-3)

To a stirred solution of 1-2 (2.58 g, 12.0 mmol) and Pd(PPh$_3$)4 (416 mg, 4.32 mmol) in toluene (25 mL) under 1 atm argon was added 2M Na$_2$CO$_3$ (12.5 mL, 25 mmol) followed by 1-1(2.4 g, 14.4 mmol) dissolved in CH$_3$OH (5 mL). The mixture was heated to 80° C. for 3.0 hours. The reaction was allowed to cool to ambient temperature and then 2M Na$_2$CO$_3$ (60 mL, 120 mmol) and CH$_2$Cl$_2$ (150 mL) were added. The organic portion was separated, dried (MgSO$_4$) and concentrated. Flash chromatography (silica gel, CHCl$_3$) gave 1-3 as a white solid.

TLC R$_f$=0.71 (silica gel, 40% EtOAc/hexanes).

$^1$H NMR (300 MHz, CD$_3$OD) δ 8.51 (s, 1H), 8.27 (dd, J=2.2, 8.2 Hz, 1H), 8.18 (d, J=8.3 Hz, 2H), 7.97 (d, J=7.5 Hz, 1H), 7.66 (m,3H), 39.8 (s,3H).

3'-Amino-biphenyl-4-carboxylic acid methyl ester (1-4)

A mixture of 1-3 (1.6 g, 6.2 mmol) and 10% Pd/carbon (1.0 g) in EtOH (100 mL) was stirred under a balloon of hydrogen for 1.0 hour.

Filtration and evaporative removal of the solvent provided 1-4 as a white solid.

TLC R$_f$=0.13 (silica gel, 25% EtOAc/hexanes).

1H NMR (300 MHz, CD$_3$OD) δ 8.05 (d, J=8.6 Hz, 2H), 7.68 (d, J=8.5 Hz, 2H), 7.23 (t, J=7.6 Hz, 1H), 7.07 (m, 2H), 6.81 (dd, J=1.0, 7.8 Hz, 1H), 3.92 (s,3H).

3'-Amino-biphenyl-4-carboxylic acid hydrochloride (1-5)

A mixture of 1-4 (500 mg, 2.20 mmol) and 6N HCl (50 mL) was heated at 60° C. for 20 h. Evaporative removal of the solvent provided 1-5 (530 mg, 96%) as a white solid.

1H NMR (300 MHz, CD$_3$OD) δ 8.15 (d, J=8.6 Hz, 2H), 7.78 (m,3H), 7.66 (t, J=8.0 Hz, 2H), 7.41 (d, J=7.8 Hz, 1H).

3'(Pyrimidin-2-yl-amino)-biphenyl-4-carboxylic acid trifluoroacetate (1-7)

A solution of 1-5 (700 mg, 2.80 mmol) and bromide 1-6 (446 mg, 2.80 mmol) in 1-methyl-2-pyrrolidinone (6 mL) was heated at 180° C. in a sealed tube for 0.5 hour. The cooled reaction mixture was purified by preparative HPLC (95:5:0.1 then 30:70:0.1 H$_2$O/CH$_3$CN/TFA) to afford 1-7 as a brown solid.

1H NMR (300 MHz, CD$_3$OD) δ 8.46 (d, J=4.9 Hz, 2H), 8.11 (d, J=6.6 Hz, 2H), 8.02 (m, 1H), 7.75 (d, J=8.8 Hz, 2H), 7.68 (m, 1H), 7.41 (m, 2H), 6.85 (t, J=4.9 Hz, 1H).

3'(Pyrimidin-2-yl-amino)-biphenyl-4-carbonyl-2(S)-phenylsulfonylamino-β-alanine tert-butyl ester (1-9)

A mixture of 1-7 (150 mg, 0.370 mmol), 1-8 (125 mg, 0.370 mmol) (for preparation, see patent application WO 95/32710 which published on Dec. 7, 1995), BOP (164 mg, 0.370 mmol), and NMM (0.204 mL, 1.85 mmol) in DMF (3 mL) was stirred for 72 hours. The mixture was diluted with ethyl acetate, washed with H$_2$O, sat. Na$_2$CO$_3$, brine, and dried over MgSO$_4$. Following evaporative removal of the solvent, the residue was chromatographed (silica gel, 75% EtOAc/hexanes) to give 1-9 as a brown solid.

TLC R$_f$=0.32 (silica gel, 75% EtOAc/hexanes).

$^1$H NMR (300 MHz, CD$_3$OD) δ 8.44 (d, J=4.6 Hz, 2H), 8.03 (s, 1H), 7.86 (d, J=8.3 Hz, 4H), 7.71(m, 3H), 7.30–7.55 (m, 5H), 6.80 (t, J=4.9 Hz, 1H), 4.17 (m, 1H), 3.71 (m, 1H), 3.54 (m, 1H), 1.25 (s, 9H).

3'-[N-(3,4,5,6-tetrahydropyrimidin-2-yl)amino]biphenyl-4-carbonyl-2(S)-phenylsulfonylamino-β-alanine (1-10)

A solution of 1-9 (175 mg, 0.305 mmol), TFA (3 mL) and CH$_2$Cl$_2$ (3 mL) was stirred at ambient temperature for 3.0 hours. The reaction was concentrated and then azeotroped with toluene (3×10 mL). The residue was dissolved in 5:1 AcOH/HCl (36 mL). 10% Pd/C (150 mg) was added and the mixture was shaken under 62 psi of hydrogen gas for 2.0 hours. Following filtration and evaporative removal of the solvent, the residue was chromatographed (silica gel, 10:1:1 EtOH/ NH$_4$OH/H$_2$O) to give 1-10 as a colorless oil.

TLC R=0.17 (silica gel, 10:1:1 EtOH/ NH$_4$OH/H$_2$O)

$^1$H NMR (300 MHz, CD$_3$OD) δ 7.86 (d, J=8.5 Hz, 4H), 7.73 (d, J=8.3 Hz, 2H), 7.64 (m, 1H), 7.42–7.59 (m, 5H), 7.28 (d, J=7.8 Hz, 2H), 4.23 (m, 1H), 3.55 (m, 1H), 3.41 (t, J=1H), 2.02 (m, 2H).

SCHEME A
Synthesis of Radioligand for SPA Assay

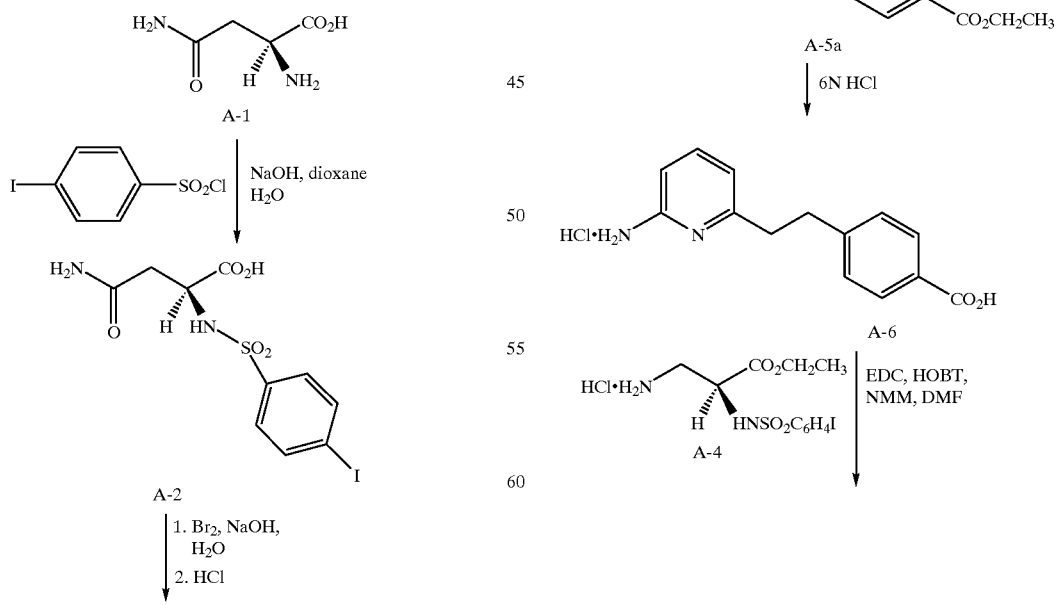

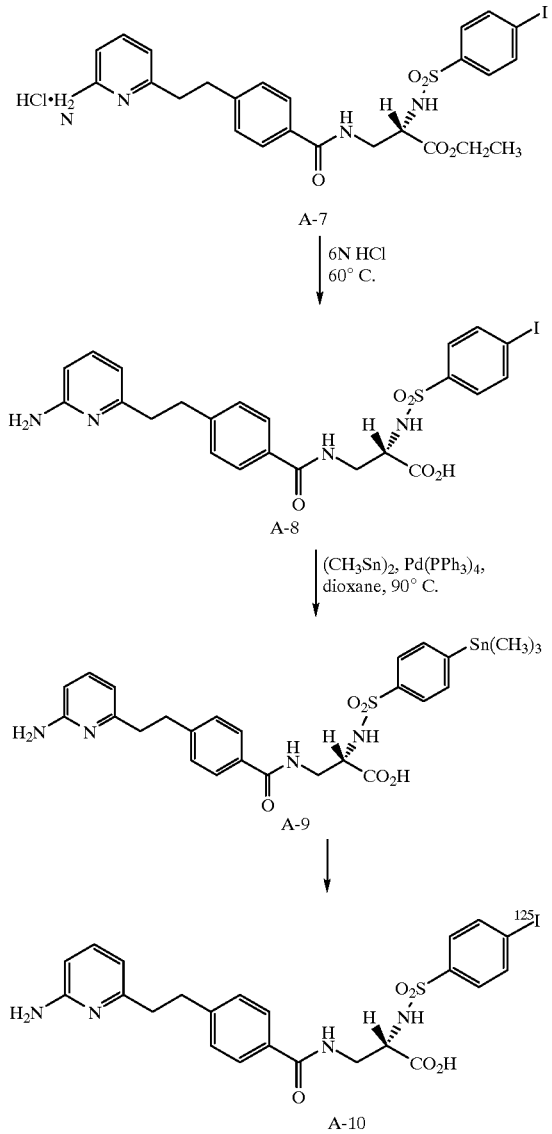

N-(4-Iodo-phenylsulfonylamino)-L-asparagine (A-2)

To a stirred solution of acid A-1 (4.39 g, 33.2 mmol), NaOH (1.49 g, 37.2 mmol), dioxane (30 ml) and $H_2O$ (30 ml) at 0° C. was added pipsyl chloride (10.34 g, 34.2 mmol). After ~5 minutes, NaOH (1.49, 37.2 mmol), dissolved in 15 ml $H_2O$, was added followed by the removal of the cooling bath. After 2.0 h, the reaction mixture was concentrated. The residue was dissolved in $H_2O$ (300 ml) and then washed with EtOAc. The aqueous portion was cooled to 0° C. and then acidified with concentrated HCl. The solid was collected and then washed with $Et_2O$ to provide acid A-2 as a white solid.

$^1$H NMR (300 MHz, $D_2O$) δ 7.86 (d, 2H, J=8 Hz), 7.48 (d, 2H, J=8 Hz) 3.70 (m, 1H), 2.39 (m, 2H).

2(S)-(4-Iodo-phenylsulfonylamino)-β-alanine (A-3)

To a stirred solution of NaOH (7.14 g, 181.8 mmol) and $H_2O$ (40 ml) at 0° C. was added $Br_2$ (1.30 ml, 24.9 mmol) dropwise over a ten minute period. After ~5 minutes, acid A-2 (9.9 g, 24.9 mmol), NaOH (2.00 g, 49.8 mmol) and $H_2O$ (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.

$^1$H NMR (300 MHz, $D_2O$) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.

$^1$H NMR (300 MHz, $CD_3OD$) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (A-5a)

A mixture of ester A-5 (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm $H_2$. After 20 h, the reaction was filtered through a celite pad and then concentrated to provide ester A-5a as a brown oil.

TLC $R^f$=0.23 (silica, 40% EtOAc/hexanes)

$^1$H NMR (300 MHz, $CDCl_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (A-6)

A suspension of ester A-5a (625 mg, 2.31 mmol) in 6N HCl (12 ml) was heated to 60° C. After ~20 h, the reaction was concentrated to give acid A-6 as a tan solid.

$^1$H NMR (300 MHz, $CD_3OD$) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodo-phenylsulfonylamino)-β-alanine (A-7)

A solution of acid 15-6 (400 mg, 1.43 mmol), amine A-4 (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. $NaHCO_3$, brine, dried ($MgSO_4$) and concentrated. Flash chromatography (silica, EtOAc then 5% isopropanol/EtOAc) provided amide A-7 as a white solid.

TLC $R_f$=0.4 (silica, 10% isopropanol/EtOAc)

$^1$H NMR (300 MHz, $CD_3OD$) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenylsulfonylamino)-β-alanine (A-8)

A solution of ester A-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/$NH_4OH$/$H_2O$) provided acid A-8 as a white solid.

TLC $R_f$=0.45 (silica, 20:20:1:1 EtOAc/EtOH/$NH_4OH$/$H_2O$)

$^1$H NMR (400 MHz, DMSO) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl)benzoyl-2(S)-(4-trimethylstannylphenylsulfonylamino-β-alanine (A-9)

A solution of iodide A-8 (70 mg, 0.1178 mmol), [(CH$_3$)$_3$Sn]$_2$ (49 μl, 0.2356 mmol), Pd(PPh$_3$)$_4$ (5 mg) and dioxane (7 ml) was heated to 90° C. After 2 h, the reaction was concentrated and then purified by preparative HPLC (Delta-Pak C$_{18}$15 μM 100A°, 40×100 mm; 95:5 then 5:95 H$_2$O/CH$_3$CN) to provide the trifluoroacetate salt. The salt was suspended in H$_2$O (10 ml), treated with NH$_4$OH (5 drops) and then lyophilized to provide amide A as a white solid.

$^1$H NMR (400 MHz, DMSO) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodophenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% H$_2$SO$_4$/MeOH was made and immediately added to the Na$^{125}$I/iodobead vial. After stirring for three minutes at room temperature, approximately 0.04–0.05 mL of NH$_4$OH was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):H$_2$O (0.1% TFA) to 90% acetonitrile (0.1% TFA):H$_2$O (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure αvβ3 and αvβ5 binding and the bone resorption inhibiting activity of the compounds of the present invention are described below.

Bone Resorption-Pit Assay

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, Ill.). Bone slices are pooled, placed in a 10% ethanol solution and refrigerated until further use.

Prior to experimentation, bovine bone slices are ultrasonicated twice, 20 minutes each in H$_2$O. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml αMEM, pH 6.9 containing 5% fetal bovine serum and 1% penicillin/streptomycin.

Long bones from 7–14 day old rabbits (New Zealand White Hare) are dissected, cleaned of soft tissue and placed in αMEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~2×10$^7$ cells/ml). A cell suspension consisting of 5×10$^{6}$/ml in αMEM containing 5% fetal bovine serum, 10 nM 1,25(OH)$_2$D$_3$, and pencillin-streptomycin is prepared. 200 ml aliquots are added to bovine bone slices (200 mm×6 mm) and incubated for 2 hrs. at 37° C. in a humidified 5% CO$_2$ atmosphere. The medium is removed gently with a micropipettor and fresh medium containing test compounds is added. The cultures are incubated for 48 hrs., and assayed for c-telopeptide (fragments of the al chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of H$_2$O, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M NH$_4$OH followed by 2×15 min ultrasonication in H$_2$O. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting IC$_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp.31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB Assay

Duong et al., *J. Bone Miner. Res.*, 8: S378 (1993) describes a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture:

1. 175 μl TBS buffer (50 mM Tris·HCl pH 7.2, 150 mM NaCl, 1% BSA, 1 mM CaCl$_2$, 1 mM MgCl$_2$).
2. 25 μl cell extract (dilute with 100 mM octylglucoside buffer to give 2000 cpm/25 μl).

3. $^{125}$I-echistatin (25 µl/50,000 cpm) (see EP 382 451).
4. 25 µl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% poly-ethyleneimine for 10 mins) were then washed with the wash buffer (50 mM Tris HCl, 1 mM CaCl$_2$/MgCl$_2$, pH 7.2). The filter was then counted in a gamma counter.

Spa Assay
Materials:
1. Wheat germ agglutinin Scintillation Proximity Beads (SPA): Amersham
2. Octylglucopyranoside: Calbiochem
3. HEPES: Calbiochem
4. NaCl: Fisher
5. CaCl$_2$: Fisher
6. MgCl$_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: αvβ3 was purified from 293 cells overexpressing αvβ3 (Duong et al., *J. Bone Min. Res.*, 8:S378, 1993) according to Pytela (*Methods in Enzymology*, 144:475, 1987)
12. Binding buffer: 50 mM HEPES, pH 7.8, 100 mM NaCl, 1 mM Ca$^{2+}$/Mg$^{2+}$, 0.5 mM PMSF
13. 50 mM octylglucoside in binding buffer: 50-OG buffer Procedure:
1. Pretreatment of SPA beads:

500 mg of lyophilized SPA beads were first washed four times with 200 ml of 50-OG buffer and once with 100 ml of binding buffer, and then resuspended in 12.5 ml of binding buffer.

2. Preparation of SPA beads and receptor mixture

In each assay tube, 2.5 µl (40 mg/ml) of pretreated beads were suspended in 97.5 µl of binding buffer and 20 µl of 50-OG buffer. 5 µl (~30 ng/l) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 µl of binding buffer and 25 µl of 50-OG buffer.

3. Reaction

The following were sequentially added into Optiplate in corresponding wells:
(i) Receptor/beads mixture (75 ml)
(ii) 25 µl of each of the following: compound to be tested, binding
buffer for total binding or A-8 for non-specific binding (final concentration 1 µM)
(iii) A-10 in binding buffer (25 µl, final concentration 40 µM)
(iv) Binding buffer (125 µl)
(v) Each plate was sealed with plate sealer from PACKARD and
incubated overnight with rocking at 4° C.
4. Plates were counted using PACKARD TOPCOUNT
5. % inhibition was calculated as follows:
A=total counts
B=nonspecific counts
C=sample counts
% inhibition=[{(A−B)−(C−B)}/(A−B)]/(A−B)×100

OCFORM Assay

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 µm nylon cell strainer. The resulting suspension was centrifuged at 350 × g for seven minutes. The pellet was resuspended, and a sample was diluted in 2% acetic acid to lyse the red cells. The remaining cells were counted in a hemacytometer. The cells were pelleted and resuspended at 1×10$^6$ cells/mL. 50 µL was added to each well of 1.8 cells to yield 50,000 cells/well and 1,25-dihydroxy-vitamin D$_3$ (D$_3$) was added to each well to a final concentration of 10 nM. The cultures were incubated at 37° C. in a humidified, 5% CO$_2$ atmosphere. After 48 h, the medium was changed. 72 h after the addition of bone marrow, test compounds were added with fresh medium containing D$_3$ to quadruplicate wells. Compounds were added again after 48 h with fresh medium containing D$_3$. After an additional 48 h., the medium was removed, cells were fixed with 10% formaldehyde in phosphate-buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

αvβ5 Attachment Assay

Duong et al., *J. Bone Miner. Res.*, 11: S290 (1996), describes a system for expressing the human αvβ5 integrin receptor.

Materials:
1. Media and solutions used in this assay are purchased from BRL/Gibco, except BSA and the chemicals are from Sigma.
2. Attachment medium: HBSS with 1 mg/ml heat-inactivated fatty acid free BSA and 2 mM CaCl$_2$.
3. Glucosaminidase substrate solution: 3.75 mM p-nitrophenyl N-acetyl-beta-D-glucosaminide, 0.1 M sodium citrate, 0.25% Triton, pH 5.0.
4. Glycine-EDTA developing solution: 50 mM glycine, 5 mM EDTA, pH 10.5.

Methods:
1. Plates (96 well, Nunc Maxi Sorp) were coated overnight at 4° C. with human vitronectin (3 ug/ml) in 50 mM carbonate buffer (pH 9/0.6), using 100 µl/well. Plates were then washed 2× with DPBS and blocked with 2% BSA in DPBS for 2h at room temperature. After additional washes (2×) with DPBS, plates were used for cell attachment assay.
2. 293 (αvβ5) cells were grown in MEM media in presence of 10% fetal calf serum to 90% confluence. Cells were then lifted from dishes with 1× Trypsin/EDTA and washed 3× with serum free MEM. Cells were resuspended in attachment medium (3×10$^5$ cells/ml).
3. Test compounds were prepared as a series of dilutions at 2× concentrations and added as 50 µl/well. Cell suspension was then added as 50 μl/well. Plates were incubated at 37° C. with 55 CO₂ for 1 hour to allow attachment.

4. Non-adherent cells were removed by gently washing the plates (3×) with DPBS and then incubated with glucosaminidase substrate solution (100 μl/well), overnight at room temperature in the dark. To quantitate cell numbers, standard curve of glucosaminidase activity was determined for each experiment by adding samples of cell suspension directly to wells containing the enzyme substrate solution.

5. The next day, the reaction was developed by addition of 185 μl/well of glycine/EDTA solution and reading absorbance at 405 nm using a Molecular Devices V-Max plate reader. Average test absorbance values (4 wells per test samples) were calculated. Then, the number of attached cells at each drug concentration was quantitated versus the standard curve of cells using the Softmax program.

EXAMPLE OF A PHARMACEUTICAL FORMULATION

As a specific embodiment of an oral composition, 100 mg of a compound of the present invention are formulated with sufficient finely divided lactose to provide a total amount of 580 to 590 mg to fill a size O hard gel capsule.

Representative compounds of the present invention were tested and found to bind to human αvβ3 integrin. These compounds are generally found to have IC$_{50}$ values less than about 100 nM in the SPA assay.

Representative compounds of the present invention were tested and generally found to inhibit ≧50% the attachment of αvβ5 expressing cells to plates coated with vitronectin at concentrations of about 1 μM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

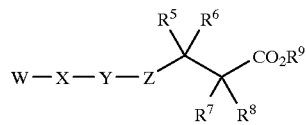

wherein W is selected from the group consisting of a 5- or 6-membered monocyclic aromatic or nonaromatic ring system having 1, 2, 3 or 4 heteroatoms selected from the group consisting of N, O, and S wherein the ring nitrogen atoms are unsubstituted or substituted with one R$^1$ substituent and the ring carbon atoms are unsubstituted or substituted with one or two R$^1$ substituents, and a 9- to 1 4-membered polycyclic ring system, wherein one or more of the rings is aromatic, and wherein the polycyclic ring system has 1, 2, 3 or 4 heteroatoms selected from the group consisting of N, O, and S wherein the ring nitrogen atoms are unsubstituted or substituted with one R$^1$ substituent and the ring carbon atoms are unsubstituted or substituted with one or two R$^1$substituents;

X is selected from the group consisting of

—(CH$_2$)$_v$—, and

—(CH$_2$)$_v$NR$^4$(CH$_2$)$_v$—; wherein any methylene (CH$_2$) carbon atom, other than in R$^4$, is either unsubstituted or substituted with one or two R$^3$ substitutents;

Y is

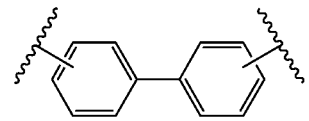

wherein the biphenyl ring system is either unsubstituted or substituted with one or more R$^1$ substituents;

Z is selected from the group consisting of

—CH$_2$CH$_2$— and —CH═CH—, wherein either carbon atom can be substituted by one or two R$^3$ substituents;

each R$^1$ is independently selected from the group consisting of hydrogen, halogen, C$_{1-10}$ alkyl, C$_{3-8}$ cycloalkyl, C$_{3-8}$ cycloheteroalkyl, C$_{3-8}$ cycloalkyl C$_{1-6}$ alkyl, C$_{3-8}$ cycloheteroalkyl C$_{1-6}$ alkyl, aryl, aryl C$_{1-8}$ alkyl, amino, amino C$_{1-8}$ alkyl, C$_{1-3}$ acylamino, C$_{1-3}$ acylamino C$_{1-8}$ alkyl, (C$_{1-6}$ alkyl)$_p$amino, (C$_{1-6}$ alkyl)$_p$ amino C$_{1-8}$ alkyl, C$_{1-4}$ alkoxy, C$_{1-4}$ alkoxy C$_{1-6}$ alkyl, hydroxycarbonyl, hydroxycarbonyl C$_{1-6}$ alkyl, C$_{1-3}$ alkoxycarbonyl, C$_{1-3}$ alkoxycarbonyl C$_{1-6}$ alkyl, hydroxycarbonyl- C$_{1-6}$ alkyloxy, hydroxy, hydroxy C$_{1-6}$ alkyl, C$_{1-6}$ alkyloxy-C$_{1-6}$ alkyl, nitro, cyano, trifluoromethyl, trifluoromethoxy, trifluoroethoxy, C$_{1-8}$ alkyl-S(O)$_p$, (C$_{1-8}$ alkyl)$_p$ aminocarbonyl, C$_{1-8}$ alkyloxycarbonylamino, (C$_{1-8}$ alkyl)$_p$aminocarbonyloxy, (aryl C$_{1-8}$ alkyl)$_p$amino, (aryl)$_p$amino, aryl C$_{1-8}$ alkylsulfonylamino, and C$_{1-8}$ alkylsulfonylamino;

or two R$^1$ substituents, when on the same carbon atom, are taken together with the carbon atom to which they are attached to form a carbonyl group;

each R$^3$ is independently selected from the group consisting of hydrogen, aryl, C$_{1-10}$ alkyl, aryl—(CH$_2$)$_r$—O—(CH$_2$)$_s$, aryl—(CH$_2$)$_r$S(O)$_p$—(CH$_2$)$_s$,
aryl—(CH$_2$)$_r$—C(O)—(CH$_2$)$_s$,
aryl—(CH$_2$)$_r$C(O)—N(R$^4$)—(CH$_2$)$_s$,
aryl—(CH$_2$)$_r$—N(R$^4$)—C(O)—(CH$_2$)$_s$,
aryl—(CH$_2$)$_r$—N(R$^4$)—(CH$_2$)$_s$,
halogen,
hydroxyl,
oxo,
trifluoromethyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
C$_{3-8}$ cycloalkyl,
(C$_{1-6}$ alkyl)$_p$amino,
amino C$_{1-6}$ alkyl,
arylaminocarbonyl,
aryl C$_{1-5}$ alkylaminocarbonyl,
aminocarbonyl,
aminocarbonyl C$_{1-6}$ alkyl,
hydroxycarbonyl,
hydroxycarbonyl C$_{1-6}$ alkyl,
HC≡C—(CH$_2$)$_t$—,
C$_{1-6}$ alkyl—C≡C—(CH$_2$)$_t$—,
C$_{3-7}$ cycloalkyl—C≡C—(CH$_2$)$_t$—,
aryl—C≡C—(CH$_2$)$_t$—,
C$_{1-6}$ alkylaryl—C≡C—(CH$_2$)$_t$—,
CH$_2$=CH—(CH$_2$)$_t$—,
C$_{1-6}$ alkyl—CH=CH—(CH$_2$)$_t$—,
C$_{3-7}$ cycloalkyl—CH=CH—(CH$_2$)$_t$—,
aryl—CH=CH—(CH$_2$)$_t$—,
C$_{1-6}$ alkylaryl—CH=CH—(CH$_2$)$_t$—,
C$_{1-6}$ alkyl—SO$_2$—(CH$_2$)$_t$—,
C$_{1-6}$ alkylaryl—SO$_2$—(CH$_2$)$_t$—,
C$_{1-6}$ alkoxy,
aryl C$_{1-6}$ alkoxy,
aryl C$_{1-6}$ alkyl,
(C$_{1-6}$ alkyl)$_p$amino C$_{1-6}$ alkyl,
(aryl)$_p$amino,
(aryl)$_p$amino C$_{1-6}$ alkyl,
(aryl C$_{1-6}$ alkyl)$_p$amino,
(aryl C$_{1-6}$ alkyl)$_p$amino C$_{1-6}$ alkyl,
arylcarbonyloxy,
aryl C$_{1-6}$ alkylcarbonyloxy,
(C$_{1-6}$ alkyl)$_p$aminocarbonyloxy,
C$_{1-8}$ alkylsulfonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonyl amino C$_{1-6}$ alkyl,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino ,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl;
or two R$^3$ substituents, when on the same carbon atom are taken together with the carbon atom to which they are attached to form a carbonyl group or a cyclopropyl group,
wherein any of the alkyl groups of R$^3$ are either unsubstituted or substituted with one to three R$^1$ substituents, and provided that each R$^3$ is selected such that in the resultant compound the carbon atom or atoms to which R$^3$ is attached is itself attached to no more than one heteroatom;
each R$^4$ is independently selected from the group consisting of
hydrogen,
aryl,
aminocarbonyl,
C$_{3-8}$ cycloalkyl,
amino C$_{1-6}$ alkyl,
(aryl)$_p$aminocarbonyl,
(aryl C$_{1-5}$ alkyl)$_p$aminocarbonyl,
hydroxycarbonyl C$_{1-6}$ alkyl,
C$_{1-8}$ alkyl,
aryl C$_{1-6}$ alkyl,
(C$_{1-6}$ alkyl)$_p$amino C$_{2-6}$ alkyl,
(aryl C$_{1-6}$ alkyl)$_p$amino C$_{2-6}$ alkyl,
C$_{1-8}$ alkylsulfonyl,
C$_{1-8}$ alkoxycarbonyl,
aryloxycarbonyl,
aryl C$_{1-8}$ alkoxycarbonyl,
C$_{1-8}$ alkylcarbonyl,
arylcarbonyl,
aryl C$_{1-6}$ alkylcarbonyl,
(C$_{1-8}$ alkyl)$_p$aminocarbonyl,
aminosulfonyl,
C$_{1-8}$ alkylaminosulfonyl,
(aryl)$_p$aminosulfonyl,
(aryl C$_{1-8}$ alkyl)$_p$aminosulfonyl,
arylsulfonyl,
arylC$_{1-6}$ alkylsulfonyl,
C$_{1-6}$ alkylthiocarbonyl,
arylthiocarbonyl, and
aryl C$_{1-6}$ alkylthiocarbonyl,
wherein any of the alkyl groups of R$^4$ are either unsubstituted or substituted with one to three R$^1$ substituents;

$R^5$ and $R^6$ are each independently selected from the group
consisting of
hydrogen,
$C_{1-10}$ alkyl,
aryl,
aryl—$(CH_2)_r$—O—$(CH_2)_s$,
aryl—$(CH_2)_r$S(O)$_p$—$(CH_2)_s$,
aryl—$(CH_2)_r$—C(O)—$(CH_2)_s$,
aryl—$(CH_2)_r$—C(O)—N($R_4$)—$(CH_2)_s$,
aryl—$(CH_2)_r$—N($R_4$)—C(O)—$(CH_2)_s$,
aryl—$(CH_2)_r$—N($R^4$)—$(CH_2)_s$,
halogen,
hydroxyl,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
$C_{3-8}$ cycloalkyl,
($C_{1-6}$ alkyl)$_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy,
aryl $C_{1-6}$ alkyl,
($C_{1-6}$ alkyl)$_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl;
or $R^5$ and $R^6$ are taken together with the carbon atom
to which they are attached to form a carbonyl group,
wherein any of the alkyl groups of $R^5$ or $R^6$ are either
unsubstituted or substituted with one to three $R^1$
substituents,
and provided that each $R^5$ and $R^6$ are selected such that in
the resultant compound the carbon atom to which $R^5$
and $R^6$ are attached is itself attached to no more than
one heteroatom;
$R^7$ and $R^8$ are each independently selected from the group
consisting of
hydrogen,
$C_{1-10}$ alkyl,
aryl,
aryl—$(CH_2)_r$—O—$(CH_2)_s$,
aryl—$(CH_2)_r$S(O)$_p$—$(CH_2)_s$,
aryl—$(CH_2)_r$—C(O)—$(CH_2)_s$,
aryl—$(CH_2)_r$—C(O)—N($R^4$)—$(CH_2)_s$,
aryl—$(CH_2)_r$N($R^4$)—C(O)—$(CH_2)_s$—,
aryl—$(CH_2)_r$—N($R^4$)—$(CH_2)_s$,
halogen,
hydroxyl,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
$C_{3-8}$ cycloalkyl,
($C_{1-6}$ alkyl)$_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—, $C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
arylaminocarbonylamino,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl, (aryl$)_p$aminocarbonyl $C_{1-6}$ alkyl,
(aryl $C_{1-8}$ alkyl$)_p$aminocarbonyl,
(aryl $C_{1-8}$ alkyl$)_p$aminocarbonyl $C_{1-6}$ alkyl, and
$C_{7-20}$ polycyclyl $C_{0-8}$ alkylsulfonylamino, wherein any of the alkyl groups of $R^7$ and $R^8$ are either unsubstituted or substituted with one to three $R^1$ substituents, and provided that each $R^7$ and $R^8$ are selected such that in the resultant compound the carbon atom to which $R^7$ and $R^8$ are attached is itself attached to no more than one heteroatom;

$R^9$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;

wherein each p is independently an integer from 0 to 2;
each r is independently an integer from 1 to 3;
each s is independently an integer from 0 to 3;
each t is independently an integer from 0 to 3; and
each v is independently an integer from 0 to 6;
and the pharmaceutically acceptable salts thereof.

2. The compound of claim 1 wherein W is selected from the group consisting of

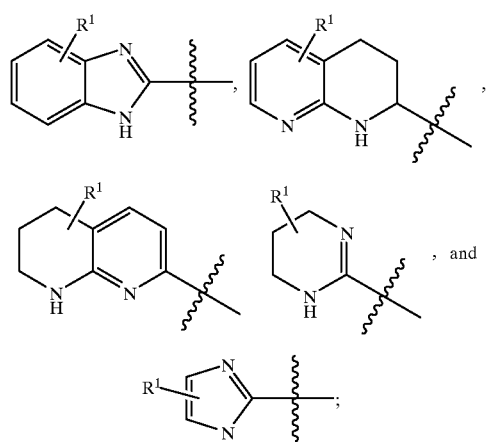

Y is

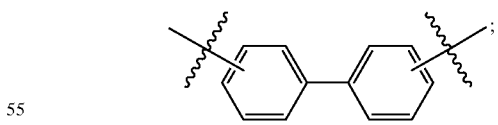

and
Z is selected from the group consisting of

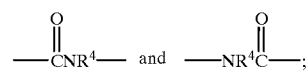

and $R^1$ and $R^4$ are as defined in claim 1.

3. The compound of claim 2 wherein W is selected from the group consisting of

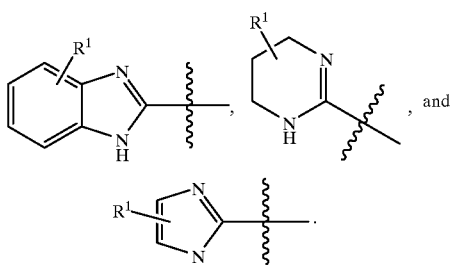

4. The compound of claim 3 wherein W is selected from the group consisting of

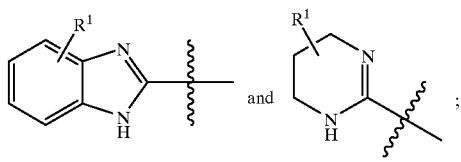

Z is

and
each v is independently an integer from 0 to 2.

5. The compound of claim 4 wherein each $R^3$ is independently selected from the group consisting of
hydrogen,
fluoro,
trifluoromethyl,
aryl,
$C_{1-8}$ alkyl,
aryl$C_{1-6}$ alkyl
hydroxyl,
oxo,
arylaminocarbonyl,
aryl $C_{1-5}$ alkylaminocarbonyl,
aminocarbonyl, and
aminocarbonyl $C_{1-6}$ alkyl;
and each $R^4$ is independently selected from the group consisting of
hydrogen,
aryl,
$C_{3-8}$ cycloalkyl,
$C_{1-8}$ alkyl,
$C_{1-8}$ alkylcarbonyl,
arylcarbonyl,
$C_{1-6}$ alkylsulfonyl,
arylsulfonyl,
aryl$C_{1-6}$alkylsulfonyl,
aryl$C_{1-6}$alkylcarbonyl,
$C_{1-8}$alkylaminocarbonyl,
aryl$C_{1-5}$alkylaminocarbonyl,
aryl$C_{1-8}$alkoxycarbonyl, and
$C_{1-8}$alkoxycarbonyl.

6. The compound of claim 5 wherein $R^6$, $R^7$, and $R^8$ are each hydrogen and $R^5$ is selected from the group consisting of
hydrogen,
aryl,
$C_{1-8}$ alkyl,
aryl—C≡C—$(CH_2)_t$—,
aryl $C_{1-6}$ alkyl,
$CH_2$=CH—$(CH_2)_t$—, and
HC≡C—$(CH_2)_t$—.

7. The compound of claim 6 wherein $R^9$ is selected from the group consisting of hydrogen, methyl, and ethyl.

8. The compound of claim 7 wherein $R^9$ is hydrogen.

9. The compound of claim 5 wherein $R^5$, $R^6$, and $R^8$ are each hydrogen and $R^7$ is selected from the group consisting of
hydrogen,
aryl,
$C_{1-8}$ alkylcarbonylamino,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
arylaminocarbonylamino,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino, and
aryl $C_{1-6}$ alkylthiocarbonylamino $C_{1-6}$ alkyl.

10. The compound of claim 9 wherein $R^7$ is selected from the group consisting of
hydrogen,
aryl, $C_{1-8}$ alkylcarbonylamino, aryl $C_{1-6}$ alkylcarbonylamino, arylcarbonylamino, $C_{1-8}$ alkylsulfonylamino, aryl $C_{1-6}$ alkylsulfonylamino, arylsulfonylamino, $C_{1-8}$ alkoxycarbonylamino, aryl $C_{1-8}$ alkoxycarbonylamino, arylaminocarbonylamino, $(C_{1-8}$ alkyl$)_p$aminocarbonylamino, (aryl $C_{1-8}$ alkyl$)_p$aminocarbonylamino, $(C_{1-8}$ alkyl$)_p$aminosulfonylamino, and (aryl $C_{1-8}$ alkyl$)_p$aminosulfonylamino.

11. The compound of claim 10 wherein $R^9$ is selected from the group consisting of hydrogen, methyl, and ethyl.

12. The compound of claim 11 wherein $R^9$ is hydrogen.

13. A compound selected from the group consisting of
3'-[N-(3,4,5,6-tetrahydropyrimidin-2-yl)amino]biphenyl-4-carbonyl-2(S)-phenylsulfonylamino-β-alanine,
3'-[N-(5,6,7,8-tetrahydro-[1,8]napthyridin-2-yl)amino]biphenyl-4-carbonyl-2(S)-phenylsulfonylamino-β-alanine, and
3'-[N-(pyrimidin-2-yl)-amino]biphenyl-4-carbonyl-2(S)-phenylsulfonylamino-alanine, and the pharmaceutically acceptable salts thereof.

14. A pharmaceutical composition comprising a compound according to claim 1 and a pharmaceutically acceptable carrier.

15. The composition of claim 14 which further comprises an active ingredient selected from the group consisting of
   a) an organic bisphosphonate or a pharmaceutically acceptable salt or ester thereof,
   b) an estrogen receptor modulator,
   c) a cytotoxic/antiproliferative agent,
   d) a matrix metalloproteinase inhibitor,
   e) an inhibitor of epidermal-derived, fibroblast-derived, or platelet-derived growth factors,
   f) an inhibitor of VEGF,
   g) an inhibitor of Flk-1/KDR, Flt-1, Tck/Tie-2, or Tie-1,
   h) a cathepsin K inhibitor,
   i) an inhibitor of osteoclast proton ATPase, and
   j) a prenylation inhibitor, such as a farnesyl transferase inhibitor or a geranylgeranyl transferase inhibitor or a dual farnesyl/geranylgeranyl transferase inhibitor; and mixtures thereof.

16. The composition of claim 15 wherein said active ingredient is selected from the group consisting of
   a) an organic bisphosphonate or a pharmaceutically acceptable salt or ester thereof,
   b) an estrogen receptor modulator,
   c) a cathepsin K inhibitor, and
   d) an inhibitor of osteoclast proton ATPase; and mixtures thereof.

17. The composition of claim 16 wherein said organic bisphosphonate or pharmaceutically acceptable salt or ester thereof is alendronate monosodium trihydrate.

18. A method of eliciting an integrin receptor antagonizing effect in a mammal in need thereof, comprising administering to the mammal a therapeutically effective amount of a compound according to claim 1.

19. The method of claim 18 wherein the integrin receptor antagonizing effect is an αvβ3 antagonizing effect.

20. The method of claim 19 wherein the αvβ3 antagonizing effect is selected from the group consisting of inhibition of bone resorption, osteoporosis, restenosis, angiogenesis, diabetic retinopathy, macular degeneration, inflammation, inflammatory arthritis, viral disease, tumor growth and metastasis.

21. The method of claim 20 wherein the αvβ3 antagonizing effect is the inhibition of bone resorption.

22. The method of claim 18 wherein the integrin receptor antagonizing effect is an αvβ5 antagonizing effect.

23. The method of claim 22 wherein the αvβ5 antagonizing effect is selected from the group consisting of inhibition of restenosis, angiogenesis, diabetic retinopathy, macular degeneration, inflammation, tumor growth and metastasis.

24. The method of claim 18 wherein the integrin receptor antagonizing effect is a dual αvβ3/αvβ5 antagonizing effect.

25. The method of claim 24 wherein the αvβ3/αvβ5 antagonizing effect is selected from the group consisting of inhibition of bone resorption, restenosis, angiogenesis, diabetic retinopathy, macular degeneration, inflammation, viral disease, tumor growth and metastasis.

26. The method of claim 18 wherein the integrin antagonizing effect is an αvβ6 antagonizing effect.

27. The method of claim 26 wherein the αvβ6 antagonizing effect is selected from the group consisting of inhibition of angiogenesis, inflammatory response, and wound healing.

28. A method of eliciting an integrin receptor antagonizing effect in a mammal in need thereof, comprising administering to the mammal a therapeutically effective amount of the composition of claim 14.

29. A method of treating or preventing a condition mediated by antagonism of an integrin receptor in a mammal in need thereof, comprising administering to the mammal a therapeutically effective amount of the composition of claim 14.

30. A method of inhibiting bone resorption in a mammal in need thereof, comprising administering to the mammal a therapeutically effective amount of the composition of claim 14.

31. A method of inhibiting bone resorption in a mammal in need thereof, comprising administering to the mammal a therapeutically effective amount of the composition of claim 16.

32. A method of treating or preventing osteoporosis in a mammal in need thereof, comprising administering to the mammal a therapeutically effective amount of the composition of claim 14.

33. A method of treating tumor growth in a mammal in need thereof, comprising administering to the mammal a therapeutically effective amount of the composition of claim 14.

* * * * *